United States Patent [19]

Ueno et al.

[11] 4,311,868
[45] Jan. 19, 1982

[54] PROCESS FOR CONVERTING HYDROCARBON

[75] Inventors: Tamotsu Ueno; Takehiko Takahashi; Kazuo Takada; Toshio Hidaka; Makoto Takagawa, all of Niigata, Japan

[73] Assignee: Mitsubishi Gas Chemical Company, Inc., Tokyo, Japan

[21] Appl. No.: 96,157

[22] Filed: Nov. 20, 1979

[30] Foreign Application Priority Data

Nov. 21, 1978 [JP] Japan ............................ 53/143846

[51] Int. Cl.$^3$ ............................................. C07C 5/13
[52] U.S. Cl. ................................ 585/747; 585/464; 585/530; 585/724
[58] Field of Search ............... 585/747, 530, 464, 724

[56] References Cited

U.S. PATENT DOCUMENTS

| | | | |
|---|---|---|---|
| 3,201,494 | 8/1965 | Oelderik et al. | 585/724 |
| 3,617,516 | 11/1971 | Gooswilligen | 585/747 |
| 3,678,120 | 7/1972 | Bloch | 585/747 |
| 3,830,871 | 8/1974 | Mayer et al. | 585/747 |
| 3,839,489 | 10/1974 | Mahan et al. | 585/747 |
| 4,035,286 | 7/1977 | McCawlay et al. | 585/747 |
| 4,058,575 | 11/1977 | Cahn et al. | 585/747 |
| 4,105,704 | 8/1978 | Say et al. | 585/747 |
| 4,144,282 | 3/1979 | McCawlay | 585/747 |

FOREIGN PATENT DOCUMENTS 48-402  7/1973  Japan .

*Primary Examiner*—Curtis R. Davis
*Attorney, Agent, or Firm*—Armstrong, Nikaido, Marmelstein & Kubovcik

[57] ABSTRACT

Hydrocarbon is catalytically converted by using a fluorine compound represented by the general formula $Z^+MF_6^-$, wherein Z is a hydrogen atom or a hydrogen group, and M is a niobium atom, an antimony atom or a tantalum atom as a catalyst, wherein a catalytically inactive component is settled as a heavy liquid phase or deposited as a solid in a reaction product solution from the conversion of hydrocarbon, the heavy liquid phase or the solid is removed from the reaction product solution, thereby removing substantially the catalytically inactive component therefrom, and the remaining catalytically active component is reused in the conversion of hydrocarbon. An amount of a fresh catalyst solution to be supplemented is considerably reduced by effectively reusing the catalytically active component.

20 Claims, 1 Drawing Figure

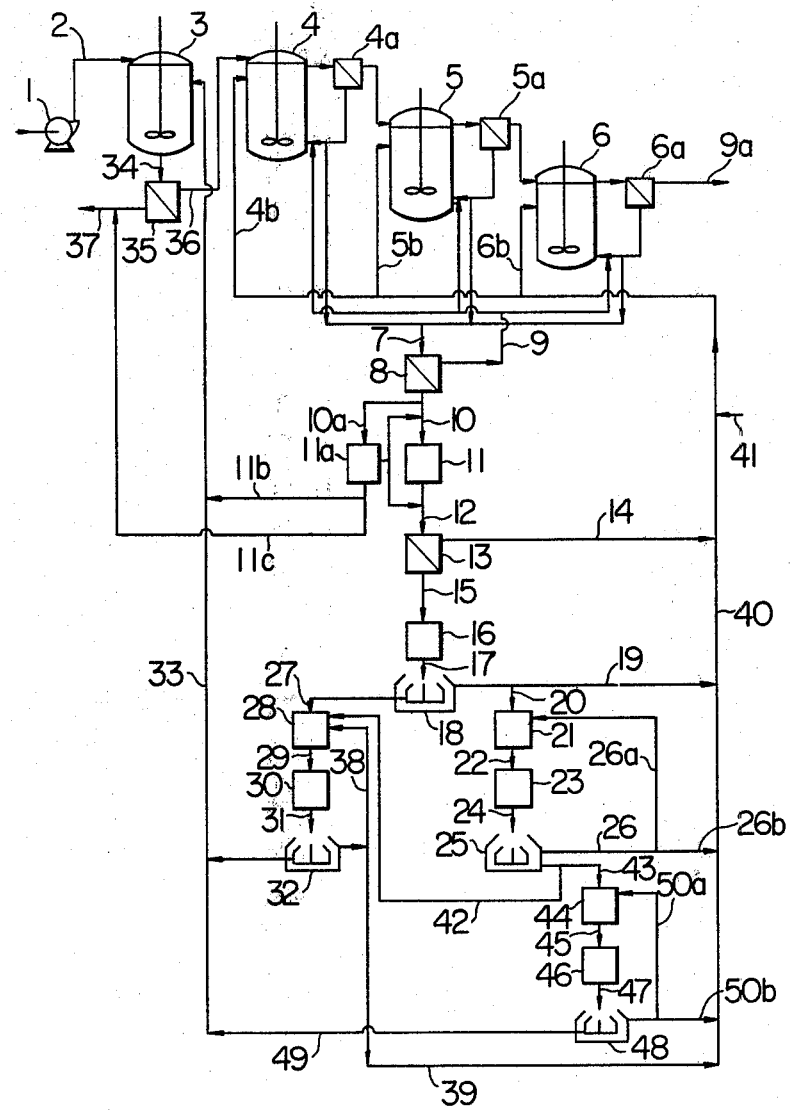

PROCESS FOR CONVERTING HYDROCARBON

This invention relates to a process for converting hydrocarbon by reuse of a purified catalyst, and more particularly to a process for converting hydrocarbon by using a catalyst of $Z^+MF_6^-$ system, where the catalyst of high activity isolated from catalytically inactive component of lowered activity is reused in the conversion of hydrocarbon.

A catalyst of hexafluoroantimonic acid system represented by the formula $Z^+SbF_6^-$ is typical of the catalyst of $Z^+MF_6^-$ used in the conversion of hydrocarbon, and is well known as a Friedel-Crafts type catalyst having a high activity, and a solution of the catalyst dissolved in a diluent such as hydrogen fluoride, fluorosulfuric acid or sulfur dioxide is usually used as a catalyst liquid. Isomerization reaction of, for example, n-paraffin can be advantageously carried out at a lower temperature favorable for the production of isoparaffins by use of the catalyst of hexafluoroantimonic acid system. For example, the catalyst is well known as a particularly good catalyst for producing high octane number gasoline by isomerization of straight run light naphtha. However, though the catalyst of hexafluoroantimonic acid system has such a distinguished property, it has not been used yet in an industrial-scale production. One reason is that the catalyst of hexafluoroantimonic acid system itself is so corrosive that an expensive material of high quality, such as a high nickel-molybdenum alloy, etc. must be employed in a reactor apparatus. Another essential reason is that only catalytically inactive component of the catalyst formed during the reaction cannot be removed from a reaction product solution which includes a reaction solution in the course of reaction or a catalyst liquid after the use of catalyst, and thus a mixture of the catalytically active component and the catalytically inactive component must be taken out from the reaction system and a fresh catalyst liquid in an amount corresponding thereto must be supplemented to renew the activity of the catalyst liquid. A large amount of the catalytically active component is, however, taken out together with the catalytically inactive component at the same time, and furthermore the fresh catalyst liquid to be supplemented must be in excess only by such an amount as to correspond to the amount of the taken-out catalytically active component. That is, if only the catalytically inactive component can be removed from the reaction product solution or catalyst liquid after the use of catalyst, the catalytically active component in the reaction product solution or the catalyst liquid can be effectively reused without being taken out together with the catalytically inactive component, and consequently only a smaller amount of the fresh catalyst liquid will be supplemented.

An object of the present invention is to provide a process for converting hydrocarbon by removing substantially a catalytically inactive component from a catalyst liquid containing both catalytically active component and catalytically inactive component after the use of catalyst, or a mixture of the catalyst liquid with hydrocarbon, and reusing the catalytically active component effectively, thereby reducing an amount of fresh catalyst to be supplemented.

As a result of extensive studies of removing the catalytically inactive component from the catalyst liquid after the use of catalyst for many years, the present inventors have found that the resulting catalytically inactive component is a heavy liquid in a sludge state having a relatively high specific gravity or crystalline material, and is different in behavior from the catalytically active component, and can readily undergo separation and deposition at such a relatively high temperature that the catalytically active component cannot undergo separation and deposition, and the remaining catalytically active component of high activity can be reused, and the present invention is based on such finding.

That is, the present invention provides a process for converting hydrocarbon by using a fluorine compound represented by the general formula $Z^+MF_6^-$, wherein Z is a hydrogen atom or a hydrocarbon group, and M is a niobium atom, antimony atom or tantalum atom, as a catalyst, characterized by settling or depositing a catalytically inactive component as a heavy liquid phase or a solid in a reaction product solution from the conversion of hydrocarbon, removing the heavy liquid phase or the solid from the reaction product solution, thereby removing substantially the catalytically inactive component therefrom, and reusing the remaining catalytically active component in the conversion of hydrocarbon.

The raw material hydrocarbon to be converted according to the present invention is not particularly limited, but straight chain or branched paraffinic hydrocarbons having 1 to 8 carbon atoms and/or straight chain or branched naphthenic hydrocarbons having 3 to 8 carbon atoms are practically used. Practically preferable hydrocarbons are paraffinic hydrocarbons having 4 to 6 carbon atoms and/or naphthenic hydrocarbons having 4 to 8 carbon atoms. Typical paraffinic hydrocarbons include n-butane, isobutane, n-pentane, isopentane, n-hexane, and isohexane, and typical naphthenic hydrocarbons include cyclohexane, methylcyclopentane, methylcyclohexane, dimethylcyclohexane, ethylcyclopentane and ethylcyclohexane, and they can be used alone or in mixture. The ordinary raw material often used is in mixture.

The conversion according to the present invention is not particularly limited, but is usually directed mainly to isomerization, but can include polymerization, dehydrogenation, hydrogenation, etc. in addition to the isomerization.

Practically particularly preferable conversion of hydrocarbon is an isomerization of n-paraffins having 4 to 6 carbon atoms.

The catalyst according to the present invention is a catalyst represented by the general formula $Z^+MF_6^-$ wherein Z is a hydrogen atom or a hydrocarbon group, and M is a niobium atom, antimony atom or tantalum atom. The catalyst of hexafluoroantimonic acid system is practically most preferable among them.

The hydrocarbon group in said general formula is hydrocarbon groups originating from the raw material paraffinic hydrocarbons and naphthenic hydrocarbons, and includes, for example, an isobutyl group

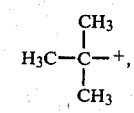

a methylcyclopentyl group

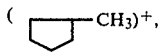

and an isopentyl group

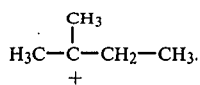

Typical catalysts are, for example, $H^+SbF_6^-$,

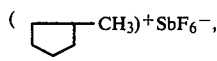

$H^+NbF_6^-$,

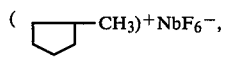

$H^+TaF_6^-$, and

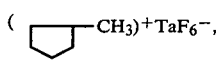

and for example, hexafluoroantimonic acid is a proton type catalyst $H^+SbF_6^-$, but the proton type catalyst is partially changed to a hydrocarbon type catalyst, (hydrocarbon group)$^+SbF_6^-$, through reaction of it with the raw material paraffinic hydrocarbons and naphthenic hydrocarbons during the conversion reaction. The hydrocarbon type catalyst whose hydrocarbon group originates from the raw material naphthenic hydrocarbon has a higher catalytic stability than the hydrocarbon type catalyst whose hydrocarbon group originates from the raw material paraffinic hydrocarbon, and thus a coexistence of even a small amount of the former hydrocarbon type catalyst is preferable. Even if only a proton type catalyst is supplied to a reactor as a catalyst, a portion of the catalyst is changed to the hydrocarbon type catalyst during the conversion reaction, and consequently there is a mixture of the proton type catalyst and the hydrocarbon type catalyst in the conversion reaction system.

A catalytic activity "A" is used as an index showing activities of a catalyst liquid, a catalytically active component and a catalytically inactive component, obtained from actual isomerization of n-hexane using these catalyst liquid, catalytically active component and catalytically inactive component. That is, "A" is given by the following equation:

$$A = \frac{L}{M} \cdot \frac{1}{t} \ln \frac{N_o - N_{eq}}{N_t - N_{eq}}$$

wherein:
A: catalytic activity (grams of raw material/gram of component metal × minute)
L: weight of raw material hydrocarbon containing n-hexane (gram)
M: weight of component metal (for example, Sb) in catalyst liquid (gram)
t: effective contact time (time from the start of stirring to separation into two layers made by discontinuation of stirring, minutes)
$N_o$: initial concentration of n-hexane in raw material hydrocarbon (% by weight)
$N_t$: concentration of n-hexane in hydrocarbon layer after the effective contact time of t minutes (% by weight)
$N_{eq}$: equilibrium concentration of n-hexane in hydrocarbon layer (% by weight)

According to this expression for the catalyst activity, a fresh catalyst liquid at such a concentration as usually used has a catalytic activity of about 0.50 to about 0.55 at 25° C.

The present invention is applied to a catalyst liquid of lowered activity, and the degree of lowering in the activity is not particularly limited, but in view of the economy and easy removal of the catalytically inactive component, the present invention is preferably applied to the catalytic liquid having a catalytic activity of not more than 90%, particularly preferably 20 to 80%, of the catalytic activity of a fresh catalyst liquid.

In the present invention, the reaction product solution obtained by the conversion of hydrocarbon is separated into a hydrocarbon layer and a catalyst layer. That is, the reaction product solution can be separated into two layers by leaving it standing at room temperature for a few seconds to about one minute particularly without any heating or cooling, but sometimes the separation can require about a few hours. In such case, the required time can be shortened by centrifuge, etc. Among the two layers, the light liquid phase is a hydrocarbon layer, and the heavy liquid phase is a catalyst layer.

To facilitate the successive treatment and operation, the hydrocarbon layer is removed by the ordinary liquid-liquid separation means such as decantation, etc. to retain the catalyst layer. The catalyst layer mainly contains physically dissolved hydrocarbon, hydrogen fluoride as the diluent, catalytically active component and catalytically inactive component. The concentration of component metal, for example, antimony, in the catalyst layer is usually adjusted to 5-40% by weight, preferably 19-35% by weight. If the concentration of component metal is less than 5% by weight, the catalytically inactive component will not be settled as a heavy liquid phase or deposited as a solid in the catalyst layer, whereas if it exceeds 40% by weight there will be such an increased danger that the entire catalyst layer will be changed into a gel. In both cases, the removal of the catalytically inactive component becomes ultimately difficult or impossible. If the concentration of component metal in the catalyst layer is less than 5% by weight, it is necessary to concentrate the catalyst layer, but the temperature for concentration must be not more than 100° C., because, if the temperature is above 100° C., the activity of catalytically active component will be lowered during the concentrating operation. Concentration is carried out by any of such means as (A) stripping by passage of an inert gas such as nitrogen gas, hydrogen gas or helium gas (B) concentration under a subatmospheric pressure, (C) concentration by heating under a subatmospheric pressure, and (D) concentration by heating. The means (A) is usually carried out at room temperature, but the simultaneous heating is not objectionable. The means (B) is usually carried out at −10° to 25° C., the means (C) usually at 25° to 50° C., and the means (D) usually at 25° to 100° C. Among these means, the means (A) to (C) are preferable because the catalyst layer is not exposed to a high temperature.

By keeping the catalyst layer of the specific concentration at −120° to 50° C., preferably −100° to 20° C., settlement of a heavy liquid phase or deposition of a solid takes place. If the temperature is below −120° C., there is an increased danger that the entire catalyst layer is changed into a gel, whereas, if the temperature is above 50° C., neither heavy liquid phase is formed nor solid is deposited. In both cases, the removal of the catalytically inactive component becomes very difficult or impossible.

The state of separation between the catalytically active component and the catalytically inactive component in the catalyst layer further mainly includes the following three states (a) to (c) in addition to said state. That is, the state (a) is such that the catalyst layer is separated into a light liquid phase and a relatively small amount of a heavy liquid phase in a sludge or tarry state. The light liquid phase can be obtained from the catalyst layer separated by the ordinary liquid-liquid separating means such as decantation, etc., and mainly contains both catalytically active component and catalytically inactive component, whereas the remaining heavy liquid phase mainly contains the catalytically inactive component. By further keeping the light liquid phase at −120° to 30° C., preferably −80° to 20° C., a solid will be deposited. The catalytically inactive component is mainly contained in the solid, whereas the catalytically active component is contained in a liquid phase. The heavy liquid phase in the sludge or tarry state is sent to a waste catalyst treatment step or regeneration step.

The light liquid phase after removing the solid by the ordinary solid-liquid separation means is returned to the reaction system as it is, or after being supplemented with the fresh catalyst liquid, whereas the solid is sent to the waste catalyst treatment step or regeneration step as it is, or after being subjected to repetitions of recrystallization in such a diluent as the above-mentioned hydrogen fluoride, etc. as a recrystallization solvent to enhance the content of the catalytically inactive component whereas mother liquor in the crystallization is supplemented with the fresh catalyst liquid and then is sent to reaction system. The amount of the recrystallization solvent to be used in the recrystallization, such as hydrogen fluoride, etc. is 0.1 to 2 parts by weight, preferably 0.2 to 1 part by weight per one part by weight of the solid. At the recrystallization, the temperature is kept at −120° to 30° C., preferably −80° to 20° C.

The state (b) is such that the catalyst layer separates into a light liquid phase and a relatively large amount of a heavy liquid phase. The light liquid phase is removed from the catalyst layer by the ordinary liquid-liquid separating means such as decantation, etc., and mainly contains the catalytically active component, and can be returned to the reaction system as it is, or after being supplemented with the fresh catalyst liquid. By keeping the heavy liquid phase at −120° to 30° C., preferably −80° to 20° C., a solid begins to deposit. Then, the heavy liquid phase is separated into a mother liquor and the solid by the ordinary solid-liquid separating means such as centrifuge, filtration, etc. The mother liquor mainly contains the catalytically active component, and is returned to the reaction system after being supplemented with the fresh catalyst liquid, whereas the solid is sent to the waste catalyst treatment step or regeneration step as it is or after being subjected to repetitions of recrystallization as conducted in the same manner as described above referring to said state (a).

The state (c) is such that the catalyst layer is once separated into a light liquid phase and a heavy liquid phase at about −20° C. while gradually lowering the temperature of the catalyst layer at the specific concentration, and a solid begins to deposit in the heavy liquid phase at about −65° C. while further lowering the temperature. Then, the heavy liquid phase is separated into a mother liquor and the solid by the ordinary solid-liquid separating means such as centrifuge, filtration, etc. The mother liquor mainly contains the catalytically active component and is returned to the reaction system after being supplemented with the fresh catalyst liquid. The solid is sent to the waste catalyst treatment step or regeneration step as it is, or after being subjected to repetitions of recrystallization as conducted in the same manner as described above, referring to the state (a).

In the states (a) to (c), the catalytically inactive component is sent to the waste catalyst treatment step or regeneration step, but is preferably brought into contact with the raw material hydrocarbon, before being sent to said step, to remove a very small amount of catalytic poisons such as water, sulfur and excess aromatic compounds from the raw material hydrocarbon through reaction or adsorption of these catalytic poisons.

Actually the catalytically active component and the catalytically inactive component are represented by the catalytic activity "A", and are relative to each other, and thus no distinct line can be drawn between the catalytically active component and the catalytically inactive component. Accordingly, whether the heavy liquid phase or the solid in the states (a) to (c) is reused or sent to the waste catalyst treatment step is not only determined only by the states (a) to (c), but also dependent upon the degree of the catalytic activity "A" in the respective states (a) to (c). The states (a) to (c) depend upon the composition of the raw material hydrocarbon, the temperature for depositing the solid, the history and concentration of catalyst, the temperature condition after the adjustment of concentration, etc.

Sometimes, a small amount of the catalytically inactive component in the sludge state may be settled in the course of the conversion reaction. In such case, the settled waste catalyst can be removed from the reaction system, and a fresh catalyst in an amount corresponding to the amount of the removed waste catalyst can be supplemented.

When the reaction product solution separates into the hydrocarbon layer and the catalyst layer, the catalyst layer can be treated in the presence of the hydrocarbon layer without removing the latter from the reaction product solution in the same manner as above to remove the catalytically inactive component.

The catalytically active component obtained by removing the catalytically inactive component in the manner as described above can be reused in the hydrocarbon conversion reaction as it is, or after being supplemented and renewed with the fresh catalyst. Sometimes, the catalyst to be reused has a little lower catalytic activity "A" than the fresh catalyst, but there is practically no substantial difference therebetween in the ordinary hydrocarbon conversion reaction where the reaction is carried out for a considerably long time until the residual hydrocarbon concentration reaches almost an equilibrium concentration.

The present invention will be described referring to the accompanying drawing showing one embodiment of the present invention.

FIGURE is a flow diagram showing one embodiment of the present invention.

Raw material hydrocarbon containing catalytic poisons such as water, sulfur, aromatic hydrocarbons, etc. is led to a raw material hydrocarbon purification tank 3 through a line 2 by a pump 1, where the raw material hydrocarbon is brought into contact with a catalytically inactive component to be sent to a regeneration step to remove the catalytic poisons such as water, sulfur, aromatic hydrocarbons, etc. from the raw material hydrocarbon. After the purification, the raw material hydrocarbon is led to a decantor 35 and separated into an upper layer and a lower layer. The upper layer is successively led to reactors 4, 5 and 6 through a line 36 and subjected to reaction. A fresh catalyst solution or a catalyst component supplemented with the fresh catalyst liquid is supplied to the reactors through lines 4b, 5b and 6b. Reaction product hydrocarbon leaves the reaction system through the respective decantors 4a, 5a and 6a at outlets of the respective reactors through a line 9a.

On the other hand, a mixture (reaction product solution) of a small amount of the hydrocarbon and a large amount of the catalyst component is withdrawn from the bottoms of the respective decantors 4a, 5a and 6a, and led to a decantor 8 through a line 7, or returned to the respective reactors 4, 5 and 6. In the decantor 8 the reaction product solution is separated into two layers, the upper being a hydrocarbon layer and the lower being a catalyst layer. The hydrocarbon layer is returned to any one of the reactors through a line 9. When a liquid in a sludge or tarry state separates from the catalyst layer in the decantor 8, the catalyst layer is led to a separator 11a through a line 10a, where the sludge, etc. are separated from the catalyst layer, and the upper layer is led to a pretreatment tank 11 or a decantor 13. As the sludge, the lower layer from the decantor 11a is led to the raw material hydrocarbon purification tank 3 through a line 11b and a line 33, or led to a regeneration step or waste catalyst treatment step through a line 11c and a line 37.

On the other hand, the catalyst layer from the decantor 8 is led to the pretreatment tank 11 through a line 10, where it is adjusted to a desired concentration of component metal. The catalyst layer at the desired specific concentration is led to a decantor 13 through a line 12.

When the catalyst layer separates into a light liquid phase and a heavy liquid phase, they are separated from each other in the decantor 13. The light liquid phase mainly contains a catalytically active component, and is withdrawn through a line 14. When the catalyst layer does not separate into the two layers, the catalyst layer is led to a crystallization tank 16 through a line 15. The heavy liquid phase withdrawn from the decantor 13 is led to the crystallization tank 16 through the line 15. The heavy liquid phase or the unseparated catalyst layer is kept at a specific temperature in the crystallization tank 16 to deposit a solid, and then led to a centrifugal separator 18 through a line 17, where it is separated into the solid and a mother liquor. The mother liquor is withdrawn through a line 19 and/or led to a concentration tank 21 through a line 20, where it is concentrated. The concentrated liquid is then led to a crystallization tank 23 through a line 22, where it is cooled to deposit a solid, and further led to a centrifugal separator 25 through a line 24, where it is separated into the solid and a mother liquor. The mother liquor is withdrawn through a line 26 and led to the concentration tank 21 through a line 26a and/or discharged through a line 26b. The solid separated in the centrifugal separator 18 is led to a recrystallization step. That is, the solid separated in the centrifugal separator 18 is led to a dissolution tank 28 through a line 27, where it is dissolved in a recrystallization solvent such as hydrogen fluoride, etc. The resulting solution is led to a crystallization tank 30 through a line 29 and cooled to deposit a crystal, and further led to a centrifugal separator 32 through a line 31, where it is separated into the solid and a mother liquor. The solid is led to the raw material hydrocarbon purification tank 3 through the line 33 and used to separate the catalytic poisons such as water, sulfur, excess aromatic hydrocarbons, etc. contained in the raw material hydrocarbon. The liquid in the raw material hydrocarbon purification tank 3 is led to the decantor 35 through the line 34, where it is separated into a raw material hydrocarbon layer as an upper layer and a catalytically inactive component (waste catalyst) that has reacted with the catalytic poisons or adsorbed the catalytic poisons as a lower layer. The raw material hydrocarbon layer is led to the reactor tank 4 through the line 36, whereas the waste catalyst as the lower layer is led to the regeneration step or the waste catalyst treatment step through the line 37.

The mother liquor separated in the centrifugal separator 32 is led to the dissolution tank 28 through a line 38 and reused as the recrystallization solvent, or withdrawn through a line 39. The solid separated in the centrifugal separator 25 is led to the dissolution tank 28 through a line 42, and recrystallized together with the solid from the centrifugal separator 18 or alone. In the latter case, the solid from the centrifugal separator 25 is led to a dissolution tank 44 through a line 43, where it is dissolved in a recrystallization solvent such as hydrogen fluoride, etc., and the resulting solution is led to a crystallization tank 46 through a line 45, where the solution is cooled to deposit a solid, and then the resulting liquid is led to a centrifugal separator 48 through a line 47, where it is separated into the solid and a mother liquor. The solid is led to the line 33 through a line 49, and further to the raw material hydrocarbon purification tank 3 through the line 33 together with the solid from the centrifugal separator 32.

The mother liquor from the centrifugal separator 48 is led to the dissolution tank 44 through a line 50a and reused as the recrystallization solvent, or discharged through a line 50b. The light liquid phase from the line 14, and mother liquors from the lines 19, 26b, 39 and 50b are joined together at the line 40, supplemented with the fresh catalyst liquid from a line 41 to renew the catalytic activity, and led to the reactors 4, 5 and 6, respectively or to at least one of these reactors.

According to the present invention, the catalytically inactive component can be substantially removed from the catalyst liquid after the use of catalyst, and the remaining catalytically active component can be effectively used. Accordingly, an amount of a fresh catalyst liquid to be supplemented can be reduced. Thus, the present invention has a very remarkable industrial significance.

The present invention will be described in detail below, referring to Examples.

REFERENCE EXAMPLE 40 ml of solutions of $SbF_5$ in hydrogen fluoride at various concentrations and 40 ml (corresponding to 28 g) of raw material hydrocarbon were charged into an autoclave (net capacity: 200 ml) provided with an electromagnetic stirrer, and catalytic activity "A" of the fresh catalysts was determined.

The composition of the raw material hydrocarbon was as follows:

| | |
|---|---|
| n-hexane | 96.3% by weight |
| isohexanes | 2.0% by weight |
| $C_6$-naphthenes | 1.7% by weight |
| benzene | 110 ppm |

Reaction conditions were as follows

| | |
|---|---|
| Temperature | 25° C. |
| Pressure of reaction system | 4 Kg/cm² gauge (pressurized with hydrogen) |
| Stirring speed | 1,000 rpm |

Isomerization reaction was 4 times repeated in the presence of the same catalyst only by replacing the hydrocarbon layer, and an average value of the catalytic activity "A" obtained from the second to fourth reactions was made catalytic activity of a fresh catalyst.

The period of one reaction was about 20 minutes, and the concentration of n-hexane in the reaction product was 35-60% by weight. The results of determination are given in the following Table 1.

TABLE 1

| | Catalytic activity of fresh catalyst | |
|---|---|---|
| Catalyst amount (g) | Sb concentration of catalyst (% by weight) | Catalytic activity "A" (g of raw material/g of Sb . min.) |
| 47 | 11.6 | 0.55 |
| 44 | 8.6 | 0.54 |
| 42 | 6.0 | 0.52 |

The catalytic activity "A" in the following Examples was determined according to the same manner as above:

EXAMPLE 1

100 G of a solution of $SbF_5$ (antimony pentafluoride) in hydrogen fluoride ($SbF_5$ concentration: 30% by weight) and the same raw material hydrocarbon as used in Reference Example but saturated with hydrogen fluoride (i.e. 128 g of raw material hydrocarbon and 0.07 g of hydrogen fluoride) were charged into an autoclave (net capacity: 300 ml) provided with an electromagnetic stirrer, and subjected to isomerization reaction at 25° C., while maintaining the reaction system under 4 Kg/cm² gauge by pressurizing the system with hydrogen. After the reaction was continued for 45 minutes, the composition of hydrocarbon layer reached almost an equilibrium. After the end of reaction the hydrocarbon layer was removed, and 70 g of the raw material hydrocarbon saturated with hydrogen fluoride as above mentioned was charged into the autoclave, and subjected to the reaction. The catalyst was repeatedly used by repetitions of such operations, and the catalytic activity was gradually lowered. When the catalytic activity "A" of the catalyst layer in the reaction product solution was lowered down to 0.41 (77% of the catalytic activity "A" of fresh catalyst), the reaction was discontinued, and the reaction product solution was left standing at room temperature to separate it into the hydrocarbon layer and the catalyst layer.

80 G of the catalyst layer was transferred into a test tube-type reactor (net capacity: 100 ml) made of ethylene tetrafluoride-propylene hexafluoride copolymer, which will be hereinafter referred to as FEP, and subjected to concentration at 50° C. under a subatmospheric pressure (430 mmHg) for one hour. The resulting concentrated blackish brown catalyst liquid (antimony concentration: 32% by weight) was left standing at 20° C., whereby a white solid was deposited. The white solid was filtered off, whereby about 5 g of the white solid and 37 g of blackish brown mother liquor were obtained, which had catalytic activities "A" of 0.07 and 0.44, respectively. The mother liquor was supplemented with 15 g of a solution of $SbF_5$ in hydrogen fluoride ($SbF_5$ concentration: 30% by weight) and 38 g of hydrogen fluoride as a fresh catalyst liquid to make the catalytic activity "A" 0.47, and reused in the isomerization reaction.

EXAMPLE 2

Isomerization reaction was repeated in the same manner as in Example 1, except that 2% by weight of benzene was added to the raw material hydrocarbon of Example 1, on the basis of the latter. When the catalytic activity "A" of the catalyst layer was lowered down to 0.24 (45% of the catalytic activity "A" of the fresh catalyst), the repeated use of the catalyst was discontinued. The resulting reaction product solution was left standing at room temperature to separate it into the hydrocarbon layer and the catalyst layer. The catalyst layer was colored dark violet, and 40 g of the catalyst layer was taken into a test tube made of FEP, and concentrated at 20° C. under a subatmospheric pressure (25 mmHg). It was observed that a violet tarry matter was deposited on the tube wall when the liquid volume was reduced to about ⅔ of the initial volume. When the liquid volume was reduced to ½, the concentration was discontinued, and the concentrated solution was left standing at 0° C. to separate it into a tarry heavy liquid phase and a light liquid phase. The light liquid phase and the tarry heavy liquid phase had catalytic activities "A" of 0.26 and 0.01, and weights of 13.5 g and 7.3 g, respectively.

The light liquid phase was left standing at −30° C., whereby a white solid was deposited. By filtration, 8.5 g of a mother liquor having a catalytic activity "A" of 0.35 and 5.0 g of a solid having a catalytic activity "A" of 0.11 were obtained. The mother liquor was supplemented and renewed with the fresh catalyst liquid, and reused.

EXAMPLE 3

40 G of the catalyst layer remaining in the reactor used in Example 2 was transferred into a test tube made of FEP, and kept at −32° C. for one hour while observing the inside state. After about 3 minutes, a liquid-liquid separation was started, and an upper layer was colored light yellow, and a lower layer was colored violet. Then, a violet precipitate was started to form, and successively formation of white precipitate was observed. Catalytic activity "A" of mother liquor after filtration was 0.31, and that of the mixture of both precipitates was 0.17, and the weight of the former was 22.6 g, and that of the latter was 17.4 g. The mother liquor was supplemented and renewed with the fresh catalyst liquid, and reused.

EXAMPLE 4

Isomerization reaction was repeated in the same manner as in Example 1, except that an autoclave of net capacity 500 ml was used, and 250 g of a solution of $SbF_5$ in hydrogen fluoride ($SbF_5$ concentration: 50% by weight) was charged therein.

After the catalytic activity "A" was lowered down to 0.22, a multi-stage crystallization test was conducted. That is, the reaction product solution was separated into a hydrocarbon layer and a catalyst layer, and 203.5 g of the catalyst layer of lowered activity was cooled at −75° C. to deposit a solid. By centrifuge, 175.8 g of a mother liquor and 27.7 g of the solid were separated from each other as "mother liquor 1" and "solid 1", respectively. All the amount of solid 1 was dissolved in 29 g of hydrogen fluoride at 20° C., and the resulting solution was cooled at −75° C. to deposit a solid. By centrifuge, 26.5 g of a mother liquor and 30.2 g of the solid were separated from each other as "mother liquor 2" and "solid 2", respectively.

Furthermore, all the amount of solid 2 was dissolved in 14.3 g of hydrogen fluoride at 20° C., and the resulting solution was cooled at −75° C. to deposit a solid. By centrifuge, 8.3 g of a mother liquor and 36.2 g of a solid were separated from each other as "mother liquor 3" and "solid 3", respectively. The results are shown in Table 2. $SbF_5$ balance throughout the process was 95.8%. It is seen from the results that separation of catalytically inactive component was more completely carried out by the multistage crystallization.

Mother liquor 1 was supplemented and renewed with 55 g of a solution of $SbF_5$ in hydrogen fluoride ($SbF_5$ concentration: 65% by weight) to make the catalytic activity "A" 0.409, and reused.

TABLE 2

Results of multistage crystallization test

|  | Weight (g) | Antimony concentration (% by weight) | Catalytic activity (g of raw material/ g of Sb . min.) |
|---|---|---|---|
| Catalyst liquid | 203.5 | 23.2 | 0.220 |
| Mother liquor 1 | 175.8 | 17.9 | 0.321 |
| Solution of solid 1 | 56.7* | 27.6** | 0.165 |
| Mother liquid 2 | 26.5 | 23.2 | 0.222 |
| Solution of solid 2 | 44.5* | 21.9* | 0.112 |
| Mother liquor 3 | 8.3 | 23.6 | 0.131 |
| Solution of solid 3 | 38.3* | 20.2** | 0.101 |

*weight of solution of the solid in HF
**Sb concentration in each solution of solid 1, 2 or 3.

EXAMPLE 5

A multistage continuous isomerization reaction was carried out in three autoclaves each having a net capacity of 500 ml arranged in series and each provided with an electromagnetic stirrer and a decantor at their outlets. 150 g of a solution of $SbF_5$ in hydrogen fluoride ($SbF_5$ concentration: 50%) was charged into each of the autoclaves as a catalyst, but no more catalyst was charged thereafter.

As a raw material hydrocarbon, straight run naphtha (1.8% by weight of butanes, 43.6% by weight of pentanes, 44.6% by weight of hexanes, 1.5% by weight of cyclopentane, 5.5% by weight of methylcyclopentane, 2.6% by weight of cyclohexane, 0.4% by weight of heptanes, and 220 ppm of benzene) was fed to the autoclaves at a rate of 330 g/hr under reaction conditions such as temperature: 25° C., stirring speed: 850 rpm, and pressure: 4.0 Kg/cm² gauge (pressurized with hydrogen). After operation for 180 hours, the catalyst liquids of the respective autoclaves were transferred to a crystallization apparatus made of Kel-F (trademark of chlorotrifluoro ethylene polymer) and sufficiently mixed. Total catalyst liquid amounted to 486 g. A portion of the catalyst liquid was used to determine the catalytic activity "A", and it was found to be 0.38 (which was 70% of the activity of the fresh catalyst).

The catalyst liquid was cooled at −62° C. for 4 hours, whereby a solid was deposited, and had an antimony concentration of 17% by weight. By forced filtration, 96 g of a solid and 380 g of a mother liquor were obtained. The mother liquor had a catalytic activity "A" of 0.41 and was admixed with 94 g of a solution of $SbF_5$ in hydrogen fluoride ($SbF_5$ concentration: 30% by weight), and sufficiently mixed and renewed so that the catalytic activity "A" could be 0.43 and reused (the reuse will be exemplified in Example 11).

The solid was dissolved in 24 g of hydrogen fluoride at 20° C., and the resulting solution was cooled at −75° C. to effect recrystallization, and 57 g of a solid was obtained thereby. The antimony concentration of the solid was 26.3% by weight, and the catalytic activity "A" thereof was 0.18.

EXAMPLE 6

Isomerization reaction was carried out in the same manner as in Example 1, except that 100 g of a solution of $SbF_5$ in hydrogen fluoride ($SbF_5$ concentration: 30% by weight) was used. When the catalytic activity "A" was lowered down to 0.38 (69% of the catalytic activity "A" of the fresh catalyst), repeated use of the catalyst was discontinued. 90 G of the catalyst layer from the reaction product solution was transferred into a test tube-type reactor (net capacity: 100 ml) made of FEP, and the catalyst layer was concentrated to about ½ of the initial liquid volume at 10° C. to 20° C. by streaming a nitrogen gas through the catalyst layer. The concentrated catalyst liquid had an antimony concentration of 25% by weight, and then cooled at −80° C., whereby a white solid was deposited. By filtration, 21 g of the white solid and 34 g of a mother liquor were obtained, and had catalytic activities "A" of 0.23 and 0.42, respectively. The mother liquor was reused.

EXAMPLE 7

Isomerization reaction was repeatedly carried out in the same manner as in Example 6, and when the catalytic activity "A" was lowered down to 0.36, the repeated use of the catalyst was discontinued. 80 G of a catalyst layer from the resulting reaction product solution was transferred into a test tube-type reactor (net capacity: 100 ml) made of FEP, and concentrated at 30° C. under a subatmospheric pressure (65 mmHg). After the concentration, the antimony concentration was 25% by weight. The concentrated solution was cooled at −60° C., whereby a white solid was deposited. By filtration, 21 g of the white solid and 23 g of a mother liquor were obtained, and had catalytic activities "A" of 0.21 and 0.41, respectively. The mother liquor was reused.

EXAMPLE 8

Isomerization reaction was repeatedly carried out in the same manner as in Example 6, and when the catalytic activity "A" was lowered down to 0.34, the repeated use of the catalyst was discontinued. 80 G of a catalyst layer from the reaction product solution was transferred into a test tube-type reactor (net capacity:

100 ml) made of FEP, and concentrated at 30° C. under a subatmospheric pressure (65 mmHg). After the concentration, the antimony concentration was 31% by weight.

The concentrated solution was cooled at −85° C., whereby a light liquid phase and a large amount of a heavy liquid phase were separated from each other. 4 G of the light liquid phase (catalytic activity "A" 0.45) was removed therefrom, and the remaining heavy liquid phase was maintained at −55° C., whereby a white solid was deposited. By filtration, 18 g of the solid and 14 g of a mother liquor were separated from each other. The mother liquor and the solid had catalytic activities "A" of 0.40 and 0.15, respectively. The light liquid phase and the mother liquor were joined together, and the resulting mixture was supplemented with the fresh catalyst liquid, and reused.

EXAMPLE 9

200 G of a solution of $SbF_5$ in hydrogen fluoride ($SbF_5$ concentration: 50% by weight) (catalytic activity "A": 0.55) was charged into an autoclave (net capacity: 350 ml) provided with a settling tank (net capacity: 25 ml) made of FEP at the bottom of the autoclave, and straight run naphtha (1.5% by weight of butane, 42.8% by weight of pentane, 44.5% by weight of hexane, 1.5% by weight of cyclopentane, 5.5% by weight of methylcyclopentane, 2.6% by weight of cyclohexane, 0.4% by weight of heptane, and 1.2% by weight of benzene) saturated with hydrogen fluoride was continuously supplied to the autoclave at a rate of 120 g/hr under reaction conditions such as temperature: 25° C., stirring speed: 800 rpm, and pressure 4.0 Kg/cm² gauge (pressurized with hydrogen). After a continuous operation for 150 hours, 17.8 g of brownish violet precipitate was accumulated in the settling tank.

When the resulting mother liquor was left standing at room temperature for about 3 minutes, it separated into two layers, the upper being a product hydrocarbon layer and the lower being a catalyst layer. The catalytic activity "A" of the precipitate was 0.12, whereas that of the catalyst layer was 0.36 and the amount of the catalyst layer was 222.2 g. The catalyst layer was supplemented with the fresh catalyst liquid, and reused.

EXAMPLE 10

Isomerization reaction was carried out in the same manner as in Example 9, and after a continuous operation for 100 hours, the reaction was discontinued. The reaction product solution was transferred into a vessel (net capacity: 500 ml) made of FEP, and left standing at room temperature, whereby 170 ml of a catalyst layer and 75 ml of a hydrocarbon layer were separated from each other. The entire amount of the catalyst layer and the hydrocarbon layer was kept at −45° C. for one hour while stirring at 500 rpm, whereby 43 g of a white precipitate was formed. A mother liquor freed from the white precipitate was left standing at room temperature, whereby a hydrocarbon layer and a catalyst layer were separated again from each other. The catalytic activities "A" of the precipitate and the catalyst layer freed from the precipitate were found to be 0.23 and 0.37, respectively. The catalyst layer freed from the precipitate amounted to 176 g, and was supplemented with the fresh catalyst liquid, and reused.

EXAMPLE 11

Isomerization reaction was carried out in the same manner as in Example 5 except that 474 g of the catalyst renewed in Example 5 was equally charged into the three autoclaves in place of the fresh catalyst. As the result, concentrations of remaining n-pentane and n-hexane in the reaction product solution are shown in Table 3.

TABLE 3

| | Raw material | Fresh catalyst (Ex.5) | | | Renewed catalyst (Ex. 11) | | |
|---|---|---|---|---|---|---|---|
| Time (hr) | 0 | 50 | 120 | 180 | 50 | 120 | 180 |
| n-pentane (wt%) | 24.5 | 7.4 | 7.9 | 8.7 | 7.2 | 7.6 | 8.2 |
| n-hexane (wt%) | 21.4 | 2.7 | 3.2 | 3.8 | 2.8 | 3.1 | 3.5 |

It is obvious from Table 3 that, though there are some difference between the catalytic activity "A" of the renewed catalyst and that of the fresh catalyst, there is no substantial difference in the concentrations of remaining n-pentane and n-hexane between the renewed catalyst and the fresh catalyst when used, and that the renewed catalyst can be used equally to the fresh catalyst.

Such phenomena can be always observed in the ordinary hydrocarbon conversion reaction which is carried out for a considerably long period of reaction time until the concentrations of the remaining hydrocarbons reach their equilibrium concentrations.

EXAMPLE 12

Isomerization reaction was carried out by charging 100 g of a solution of $SbF_5$ in hydrogen fluoride ($SbF_5$ concentration: 30% by weight) and 73 g of raw material hydrocarbon containing 1.3% by weight of butanes, 42.3% by weight of pentanes, 43.4% by weight of hexanes, 7.8% by weight of $C_5$–$C_7$ naphthenes, 4.4% by weight of heptanes and 0.8% by weight of benzene, saturated with hydrogen fluroide in an autoclave (net capacity: 300 ml) provided with an electromagnetic stirrer, while maintaining the reaction system at 25° C. and 4 Kg/cm² gauge by pressurizing the reaction system with hydrogen. After the reaction for 50 minutes, the composition of the hydrocarbon layer reached almost an equilibrium. After the end of reaction, the hydrocarbon layer was removed therefrom, and 73 g of the raw material hydrocarbon saturated with hydrogen fluoride as above mentioned was again charged into the autoclave and subjected to reaction. By repeating such operations, the catalyst was repeatedly used. The activity of the catalyst was gradually lowered.

When the catalytic activity "A" was lowered down to 0.38, 115 g of the catalyst layer from the resulting reaction product solution was transferred to a test tube-type vessel made of FEP, and left standing at room temperature whereby a brownish violet tarry heavy liquid phase and a light brown light liquid phase were separated from each other. After the separation of 6 g of the heavy liquid phase and 109 g of the light liquid phase, their catalytic activities "A" were determined. The heavy liquid phase had a catalytic activity "A" of 0.03, whereas the light liquid phase had that of 0.39. Then, the light liquid phase was kept at −42° C., whereby about 18 g of white precipitate was separated. The precipitate had a catalytic activity "A" of 0.18, whereas the resulting mother liquor had that of 0.42 and amounted to 82 g. The mother liquor was supplemented with 15 g of a solution of $SbF_5$ in hydrogen fluoride ($SbF_5$ concentration: 70% by weight) to make the catalytic activity "A" 0.47, and then the isomerization reaction of the raw material hydrocarbon was continued with the renewed catalyst liquid.

What is claimed is:

1. A process for converting a hydrocarbon by using a fluorine compound represented by the general formula $Z^+MF_6^-$, wherein Z is a hydrogen atom or a hydrocarbon group, and M is a niobium atom, an antimony atom or a tantalum atom, as a catalyst, which comprises separating a reaction product solution resulting from the conversion of the hydrocarbon into a hydrocarbon layer as a first light liquid phase and a catalyst layer as a first heavy liquid phase, said catalyst layer containing catalytically inactive component and catalytically active component, settling catalytically inactive component of the catalyst layer as a second heavy liquid phase, separating the second heavy liquid phase from the catalyst layer to substantially remove the catalytically inactive component, and reusing the remaining catalytically active component in the conversion of hydrocarbon.

2. A process for converting a hydrocarbon by using a fluorine compound represented by the general formula $Z^+MF_6^-$, wherein Z is a hydrogen atom or a hydrocarbon group, and M is a niobium atom, an antimony atom or a tantalum atom, as a catalyst, which comprises separating a reaction product solution resulting from the conversion of the hydrocarbon into a hydrocarbon layer as a first light liquid phase and a catalyst layer as a first heavy liquid phase, said catalyst layer containing catalytically inactive component and catalytically active component, depositing catalytically inactive component of the catalyst layer as a solid, separating the solid from the catalyst layer to substantially remove the catalytically inactive component, and reusing the remaining catalytically active compound in the conversion of hydrocarbon.

3. A process according to claim 1 or 2, wherein the catalyst layer has a concentration of component metal of 5 to 40% by weight, and the catalytically inactive component is removed from the catalyst layer.

4. A process according to claim 1 or 2, wherein the catalyst layer is concentrated to a concentration of component metal of 5 to 40% by weight at not more than 100° C., and the catalytically inactive component is removed from the catalyst layer.

5. A process according to claim 1 or 2, wherein the catalyst layer is kept at −120° C. to 50° C., thereby settling or depositing the catalytically inactive component as the second heavy liquid phase or the solid, and the second heavy liquid phase or the solid is removed from the catalyst layer.

6. A process according to claim 1, wherein the catalyst layer is separated into a second light liquid phase and said second heavy liquid phase, said second heavy liquid phase is kept at −120° C. to 30° C., thereby depositing a solid containing the catalytically inactive component, the solid is removed therefrom, and the resulting mother liquor containing the remaining catalytically active component and said second light, liquid phase containing the catalytically active component are reused.

7. A process according to claim 1, wherein the catalyst layer is separated into a second light liquid phase and said second heavy liquid phase by gradually lowering the temperature thereof, thereby cooling the catalyst layer, a solid containing the catalytically inactive component is deposited in said second heavy liquid phase by further gradually lowering the temperature, thereby cooling the heavy liquid phase, the solid is removed therefrom, and the resulting mother liquor containing the remaining catalytically active component and the second light liquid phase containing the catalytically active component are reused.

8. A process according to claim 7, wherein the cooling temperature for separating the catalyst layer into the second light liquid phase and the second heavy liquid phase is about −20° C., and the cooling temperature for starting the deposition of the solid in the second heavy liquid phase is about −65° C.

9. A process according to claim 1 or 2, wherein the catalyst layer is left standing while keeping the catalyst layer at a desired specific temperature, thereby separating the catalytically inactive component.

10. A process for converting a hydrocarbon by using a fluorine compound represented by the general formula $Z^+MF_6^-$, wherein Z is a hydrogen atom or a hydrocarbon group, and M is a niobium atom, an antimony atom or a tantalum atom, as a catalyst, which comprises removing sludge formed during the conversion of the hydrocarbon from the reaction product solution to thereby remove inactive component of the catalyst, and thereafter separating the resulting mother liquor into a hydrocarbon layer and a catalyst layer and reusing the catalyst layer.

11. A process according to claim 1, 2 or 10, wherein the raw material hydrocarbon is straight chain or branched paraffinic hydrocarbon having 1 to 8 carbon atoms, or naphthenic hydrocarbon having 3 to 8 carbon atoms.

12. A process according to claim 1, 2 or 10, wherein the conversion of hydrocarbon is isomerization, polymerization, dehydrogenation or hydrogenation of hydrocarbon.

13. A process according to claim 12, wherein the conversion of hydrocarbon is isomerization of hydrocarbon.

14. A process according to claim 1, 2 or 10, wherein the catalyst is a fluorine compound represented by $Z^+SbF_6^-$, wherein Z is a hydrogen atom or a hydrocarbon group.

15. A process according to claim 14, wherein the catalyst supplied to the reaction system is hexafluoroantimonic acid of $H^+SbF_6^-$.

16. A process according to claim 14, wherein the catalyst is (hydrocarbon group)$^+SbF_6^-$, wherein the hydrocarbon group is a group originating from the raw material paraffinic hydrocarbon and naphthenic hydrocarbon, respectively.

17. A process according to claim 14, wherein the catalyst is (hydrocarbon group)$^+SbF_6^-$, wherein the hydrocarbon group is an isobutyl group, a methylcyclopentyl group or an isopentyl group.

18. The process according to claim 1 or 2, wherein the hydrocarbon layer is separated from the catalyst layer prior to removing the catalytically inactive component from the catalyst layer.

19. A process according to claim 1, wherein the catalyst layer is separated into a second light liquid phase and said second heavy liquid phase, the second light liquid phase is kept at −120° to 30° C., thereby depositing a solid containing catalytically inactive component, the solid is removed therefrom, and the resulting liquid containing the remaining catalytically active component is reused.

20. A process according to claim 2 wherein the catalyst layer is separated into a second light liquid phase and said solid, the second light liquid phase is kept at −120° to 30° C., thereby depositing catalytically inactive component in a solid form, said solid form of catalytically inactive component is removed therefrom, and the resulting liquid containing the remaining catalytically active component is reused.

* * * * *